United States Patent [19]
Chupp

[11] Patent Number: 4,710,635
[45] Date of Patent: Dec. 1, 1987

[54] DUAL LASER EXCITATION FROM SINGLE LASER SOURCE

[75] Inventor: Vernon L. Chupp, Los Alto, Calif.

[73] Assignee: Becton, Dickinson and Company, Franklin Lakes, N.J.

[21] Appl. No.: 852,007

[22] Filed: Apr. 14, 1986

[51] Int. Cl.$^4$ ............................................. G01N 21/64
[52] U.S. Cl. .............................. 250/461.2; 250/461.1; 356/318
[58] Field of Search ............... 250/461.2, 461.1, 458.1; 356/318, 317, 301

[56] References Cited

U.S. PATENT DOCUMENTS

| | | | |
|---|---|---|---|
| 3,826,364 | 7/1974 | Bonner et al. | 209/3.1 |
| 4,071,298 | 1/1978 | Falconer | 356/73 |
| 4,284,412 | 8/1981 | Hansen et al. | 436/808 |
| 4,609,286 | 9/1986 | Sage, Jr. | 356/73 |
| 4,622,468 | 11/1986 | Stefanski et al. | 250/458.1 |

OTHER PUBLICATIONS

J. Jasny and J. Sepiol, "Nanosecond Transient Absorption Spectrophometer with Dye Laser Probe", *J. Phys. E: Sci. Instrum.*, vol. 14, No. 4, (Apr. 1981), pp. 493–497.

D. J. Arndt-Jovin, B. G. Grimwade, and T. M. Jovin, "A Dual Laser Flow Sorter Utilizing a CW Pumped Dye Laser", *Cytometry*, vol. 1, No. 2, (1980), pp. 127–131.

*Primary Examiner*—Janice A. Howell
*Assistant Examiner*—Constantine Hannaher
*Attorney, Agent, or Firm*—Richard J. Rodrick

[57] ABSTRACT

A dual laser excitation apparatus comprises a first laser for providing a first beam of light with a plurality of energy lines. A filter or wavelength disperser is included for dividing the first beam of light into two portions. One of these portions of the light beam is spectrally separated and at least one separated line is directed to a first area of illumination. A second laser is positioned to receive the other portion of the divided light beam and is adapted to be energized thereby. The second laser produces a second beam of light directed to a second area of illumination. Such a dual laser excitation apparatus is well suited for flow cytometry purposes.

22 Claims, 3 Drawing Figures

DUAL LASER EXCITATION FROM SINGLE LASER SOURCE

BACKGROUND OF THE INVENTION

1. Field of the Invention

The present invention relates to a dual laser excitation apparatus with a single laser source, and more particularly, concerns a flow cytometry apparatus for determining characteristics of cells or the like.

2. Related Information

There are many applications in which lasers are employed as light sources. One such application of lasers is in flow cytometry apparatuses. In a flow cytometry apparatus, cells or other particles are passed in a liquid flow stream so that one or more characteristics of the cells under investigation may be determined. Cellular analysis by reliance on optical investigation is a commonly used technique in flow cytometry apparatuses. Typically, an incident beam of light is directed at the stream of cells as they pass through the apparatus. The passing cells scatter the light as they pass through the light beam. Scattered light has served as a function of cell shape, index of refraction, opacity, roughness and the like. In addition, fluorescence emitted by labeled cells which have been excited as a result of passing through the excitation energy of the incident light beam is detectable for identification of specifically labeled cells. Lasers have been used as the source of the incident beam of illumination in flow cytometry apparatuses.

Multi-parameter analysis of cells is a tool which provides significantly more information about individual cells in order to understand the characteristics of such cells. One technique for improving multi-parameter analysis is the multiple fluorescence detection with respect to the cells under investigation. Although it has been known in the art that a single light source, such as a laser, may be used as an excitation source or two fluorescent labels on the cells, the increased need for multiple labels and the requirement that the absorption of the label match the wavelength of the laser has brought about development of systems which employ two lasers in order to excite two or more distinguishable fluorescent markers. Apparatuses utilizing two lasers for cellular analysis are described, for example, in U.S. Pat. Nos. 3,826,364 and 4,284,412.

Utilization of dual laser systems also permits the multi-parameter cell analysis and sorting with three or four different fluorochromes. One such dual laser system, known as the FACS 440 Cell Sorter manufactured and sold by Becton Dickinson Immunocytometry Systems, Mt. View, Calif., relies upon a common lens system for collecting fluorescence emission from all fluorochromes, after which individual colors are separated by means of appropriate combinations of dichroic filters, mirrors and beam splitters. This flow cytometry system is described in commonly assigned patent application Ser. No. 482,345, filed on Apr. 5, 1983. In order for such a flow cytometry system to obtain optimum performance in terms of signal to noise characteristics in each channel, and with minimum channel crosstalk, it is desirable that the two laser excitation sources have sufficient separation both spectrally and spatially. By spectral separation, it is meant that the second laser excitation wavelength should be outside the acceptance window of the emission filters for cells excited by the first laser.

In the flow cytometry system described in the aforementioned patent application, spatial separation is achieved by directing the two lasers so that the respective focal points on the cell stream are vertically displaced by about 200-250 microns. The pulses from the two lasers are thus time-separated. Spatial separation occurs by placing a high reflectance mirror in the optical emission path near a magnified image of the stream. This so-called split mirror is positioned so that emission from the first laser passes beyond the mirror's edge, while emission from the second laser is intercepted and reflected into an alternate path. Further spectral separation of the individual emission channels in the two spatially separated beams is accomplished by placing an appropriate dichroic in each light beam.

Adequate spectral separation of the excitation light sources has been obtained by using a visible laser, such as an argon laser, in single line mode as a primary laser, and a dye laser with a multi-line argon pump as the secondary laser. The primary laser may be adjusted to one of the visible argon lines between, for example, 457.9 nm and 514.5 nm, while the secondary laser uses a dye, such as for example, R6G which may be adjusted to output a line between 580 nm and 640 nm. For four color applications, the primary laser, which may, for example, be set at 488 nm, excites two fluorochromes, such as fluorescein isothiocyanate (FITC) and phycoerythrin (PE) which emit fluorescence at 520 nm and 575 nm, respectively. On the other hand, the dye laser, which may, for example, be set 598 nm, excites two additional stains such as Texas red (TR) and allophycocyanin (A-PC) with corresponding emission peaks at 625 nm and 660 nm, respectively.

A scheme for obtaining dual line performance from a single dye laser system is described by Arndt-Jovin et al. in "A Dual Laser Flow Sorter Utilizing a CW Pumped Dye Laser," Journal of the Society for Analytical Cytology, vol. 1, no. 2, pp. 127-131 (1980). The performance of the scheme described by Arndt-Jovin et al. cannot be expected to be as good as a dual laser system for a number of reasons. First, short wavelength line isolation is done entirely with interference filters. Such filters with spectral band widths narrow enough to isolate a single argon line usually do not have a very high transmission peak, and it cannot be expected to withstand the required power densities for long periods of time. Second, changing the wavelength of the primary line is usually not a simple external adjustment, but rather requires changing several filters, and perhaps some realignment. Finally, the method of stabilizing the two laser lines simultaneously is usually inadequate.

There are other technical problems which are associated with the use of a single dye laser system for obtaining dual line performance. Current dye laser systems use the argon laser in a multi-line mode simply because this is the way to obtain the most available power for pumping the dye. Since such a system expects a single argon laser to satisfy the requirements of both the primary and secondary laser, the efficiency of the filtering system is critical with respect to the performance characteristics. Laser amplitude stability is also a problem. The best known method for stabilizing the output of lasers is what is known as light control in which a small amount of the final output beam is picked off and continuously monitored by a detector. This signal is used as feedback for controlling the input current for the laser.

The individual output lines in a multi-line laser do not necessarily drift in the same way. Therefore, any system which spectrally splits up a single pump into two separate sources can accept feedback from only one of the final output lines as input current control. Thus, unless a special provision is made, at least one of the incident sources will be less stable than the normal dual laser system.

Previous schemes for using part of the pump for independent excitation, such as described by Arndt-Jovin et al., usually require changing several filters along with realignment for changing wavelength. Also, changing the wavelength of the short wavelength line has an impact on the dye laser performance. Moreover, narrow band interference filters usually do not withstand the high laser power densities for extended lengths of time without ultimately burning and becoming damaged, or useless.

Finally, present systems, which make no provision for independent focusing of the argon and dye optical paths onto the cell stream, result in a less than optimum focus of one of the two beams. The need for independent focus adjustment is occasioned by the substantially unequal output beam divergence of the respective pump and dye lasers. One dye laser system which is manufactured by Coherent Inc. of Palo Alto, Calif., has a pump output divergence of 0.00048 radians at 488 nm, and a dye output divergence of 0.0015 radians at 600 nm. Such a system cannot be simultaneously focused by a single lens, even a well corrected achromat.

It can be appreciated that improvements are needed in laser apparatuses wherein dual line performance results from a single dye laser system. The present invention is directed to such improvements and to the solution of the deficiencies and problems mentioned above.

SUMMARY OF THE INVENTION

The dual laser excitation apparatus of the present invention comprises a first laser for providing a first beam of light with a plurality of energy lines. Means are provided for dividing the first beam of light into two portions. Dispersive means separates spectral lines of one portion of the divided light beam and directs at least one of the spectrally separated lines to a first area of illumination. A second laser is positioned to receive the other portion of the divided light beam and is adapted to be energized thereby to produce a second beam of light directed to a second area of illumination.

In a preferred application of the apparatus of the present invention, a flow cytometry apparatus determines one or more characteristics of particles or the like flowing in a liquid stream. The flow cytometry apparatus comprises means for moving particles, substantially one at a time, in a liquid flow stream. Means provides a first beam of light with a plurality of energy lines. Means divides the first beam of light into two portions. Means separates spectral lines of one portion of the divided light beam and directs at least one of the spectrally separated lines toward the particles moving in the stream to provide a first area of illumination therefor. Means receives the other portion of the divided light beam and is energized thereby to produce a second beam of light directed toward the particles moving in the stream to provide a second area of illumination therefor. Means detects light with respect to each moving particle and associates the detected light with one or more characteristics of each particle. Further means are preferably included for intercepting and sensing a small portion of said spectrally separated lines and for adjusting said detecting means to compensate for observed intensity fluctuations.

In accordance with the principles of the present invention, the deficiencies and problems associated with the prior laser systems are overcome. As a result, the present invention provides a versatile, efficient two-line system, both lines of which are easily and independently adjustable, while utilizing a single argon laser as both a primary excitation source and as the pump for a secondary excitation source. Of particular note, the present invention realizes performance substantially equivalent to that of a full-blown dual laser system using two separate lasers, while relying on a single dye laser system plus additional optics and elements. Significant economic savings are realized by constructing a dye laser system in accordance with the present invention. The dual line system of the present invention is intended primarily for three and four color fluorescence applications where, as mentioned above, the primary line may be set at 488 nm to excite FITC and PE, and the secondary line may be set at approximately 598 nm to excite either TR or TR and A-PC. Furthermore, as an indication that the present invention represents a complete dual line system, provisions are made for the operator to be able to easily change excitation wavelengths of either the primary or secondary lines for other applications. For example, for DNA applications a commonly used stain may be excited with the 457.9 argon line. In addition, RNA content may be determined by counting reticulocytes using a known reagent which is also excited at 457.9 nm. Other applications prefer the 514.5 nm line, and so on.

Improvements in efficiency, reliability, stability and ease of wavelength adjustment result from the present invention.

DETAILED DESCRIPTION

Figure 1:
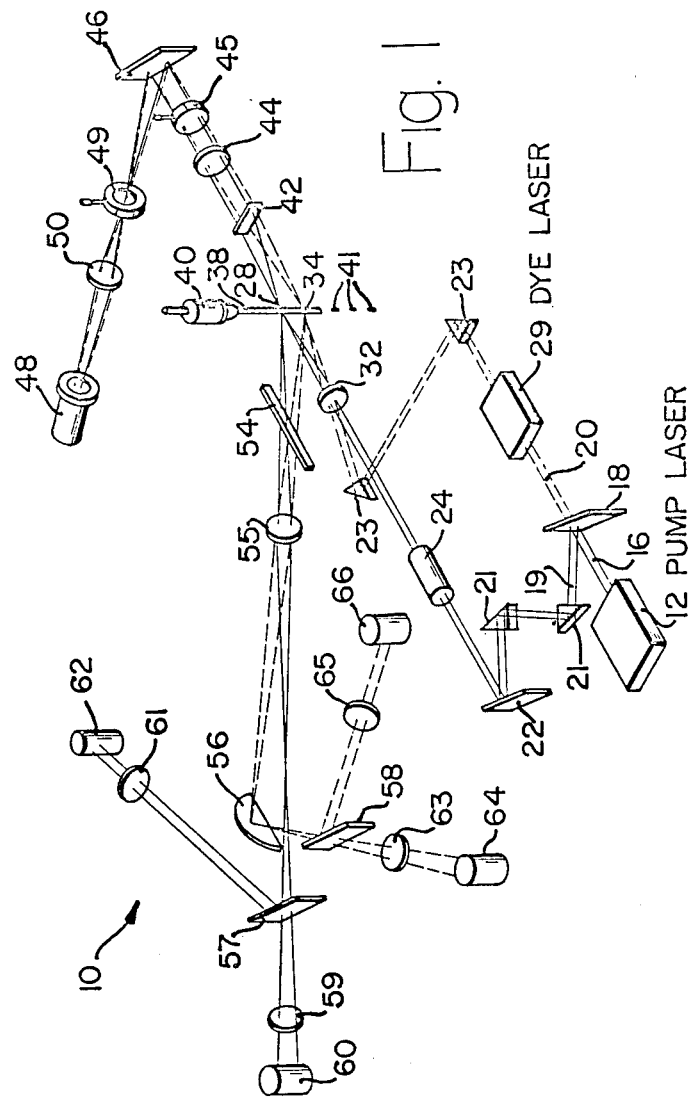
FIG. 1 is a schematic illustration of a preferred embodiment of the optical elements and light paths of a flow cytometry apparatus particularly useful for multi-parameter cellular analysis.

While this invention is satisfied by embodiments in many different forms, there is shown in the drawings and will herein be described in detail a preferred embodiment of the invention, with the understanding that the present disclosure is to be considered as exemplary of the principles of the invention and is not intended to limit the invention to the embodiment illustrated. The scope of the invention will be measured by the appended claims and their equivalents.

Figure 2:
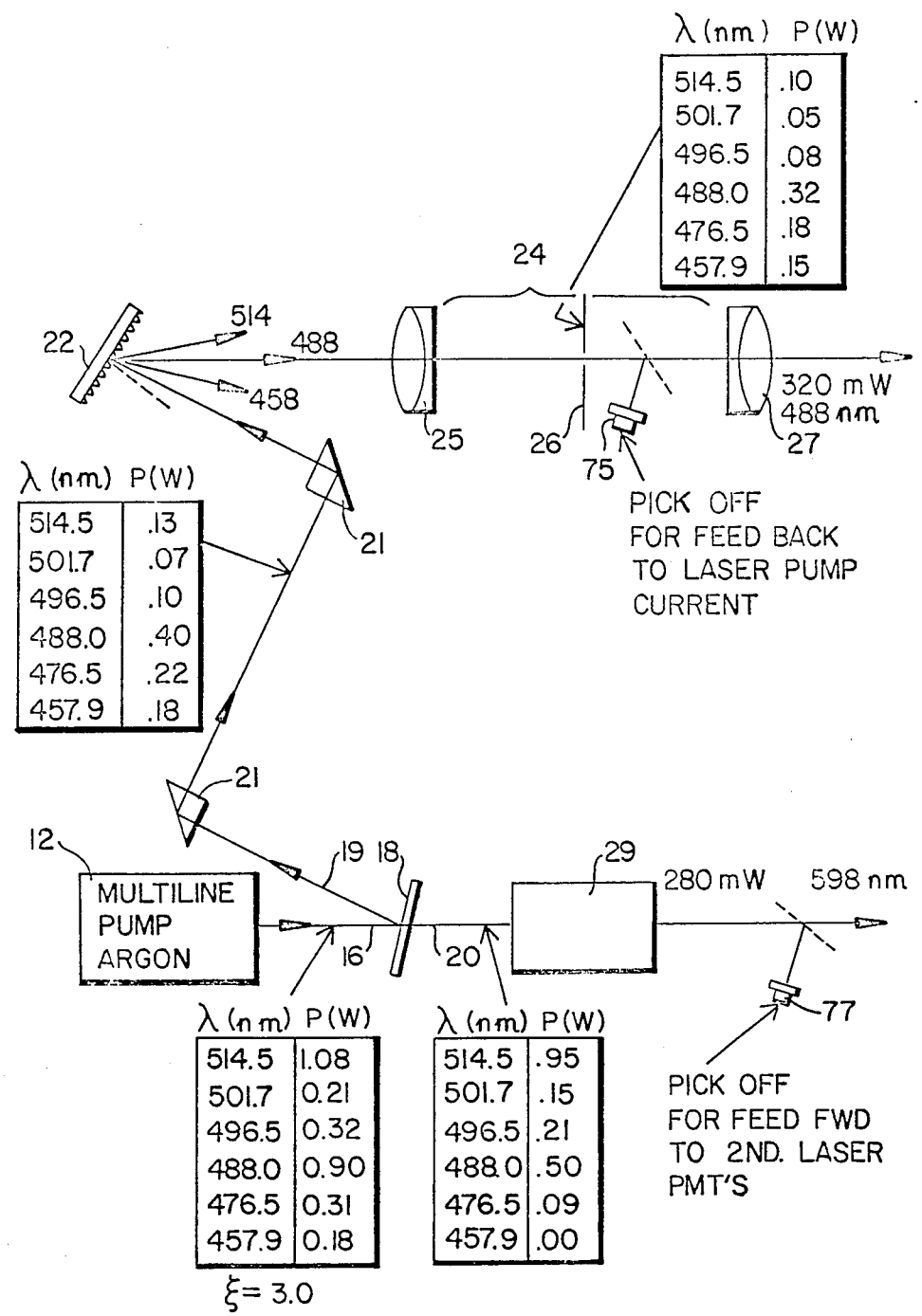
FIG. 2 is a schematic illustration of the optical and light elements of the apparatus of FIG. 1 represented in greater detail.

Referring to the drawings, and FIGS. 1 and 2 in particular, the optical and particle flow elements of a flow cytometry apparatus 10 are illustrated. The optical and flow elements of FIG. 1 represent the major components of a flow cytometry instrument for flowing particles in a liquid stream, substantially one at a time, in order to analyze those particles for specific characteristics thereof. For example, the elements of the device of FIG. 1 may be included in a FACS fluorescenceactivated cell sorter manufactured and sold by Becton Dickinson Immunocytometry Systems, Mt. View, Calif. The FACS Cell Sorter analyzes and separates cell populations on the basis of light scatter and fluorescence in a wide variety of research laboratory applications. In addition to the optical and flow elements to be described in more particular detail herein, and which may be embodied in an instrument such as the FACS Cell Sorter, other details of a cell sorting apparatus useful in conjunction with the present invention are described in U.S. Pat. No. 3,826,364. It is understood that the present invention is useful in many different types of laser applications, including flow cytometry devices, whether measuring light scatter, particle volume, fluorescence or any other optical parameters for the identification or quantification of light-related characteristics.

As illustrated in FIG. 1, light energy is provided for the present flow cytometry device by laser 12. It is preferred that laser 12 be a multi-line laser, such as an argon ion laser. For purposes of the present description, a suitable multi-line argon laser may be adjusted to provide output lines at discrete wavelengths between 457.9 and 514.5 nm. Of course, lasers at other wavelengths may also be utilized for purposes of the present invention. It is also preferred that the output of multi-line laser 12 be vertically polarized and in the TEMoo mode. These characteristics allow some of the pump lines of laser 12 to be directly available for a primary excitation line.

Figure 3:
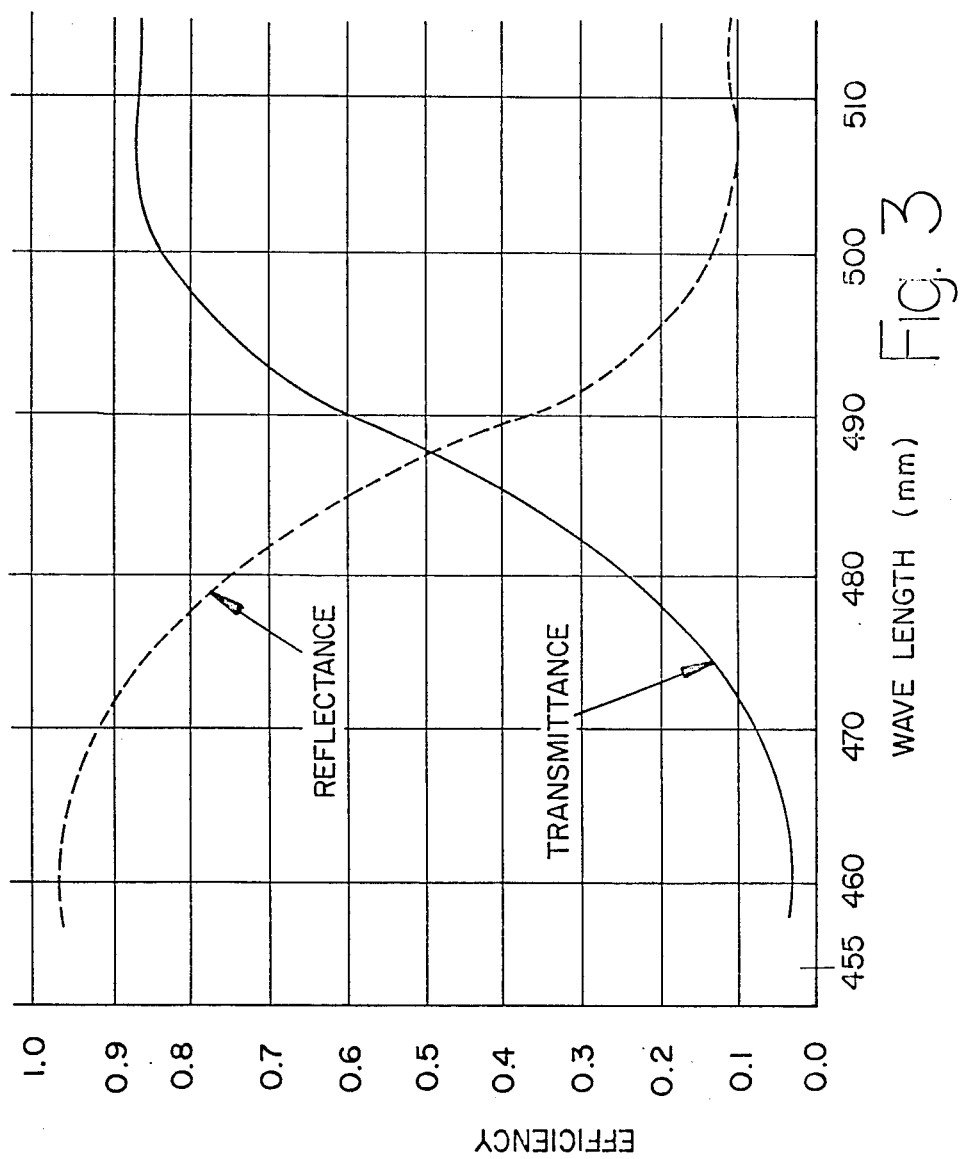
FIG. 3 is a graphic representation of the transmittance and reflectance characteristics of the dichroic element of the flow cytometry apparatus of FIG. 1.

Light beam 16 emerging from laser 12 strikes a long pass dichroic 18 which transmits some of the light and also reflects some of the light. The transmission and reflectance characteristics of the long pass dichroic are illustrated in FIG. 3, where it can be seen that both transmittance and reflectance performance of the dichroic is dependent on the wavelengths of the light striking the dichroic. Light reflected off dichroic 18 is designated by numeral 19 while light transmitted through dichroic 18 is designated by numeral 20.

In order to steer reflected light beam 19, a pair of internally reflecting turning prisms 21 is provided so that light beam 19 is directed to a light dispersing element 22. It is preferred that element 22 be a very fine-lined, deeply modulated, diffraction grating as part of a monochromator configuration for separating spectral lines from the pump laser, as will be described more fully hereinafter. From grating element 22, the diffracted argon line of interest is isolated by means of an intermediate focusing/collimating lens and slit system 24 and directed to lens 32 for focusing at region 28 in the stream of flowing particles.

Referring now to transmitted light beam 20, approximately two thirds of the pump output energy strongly favoring the longer wavelengths (as seen in FIG. 3) is transmitted and is used to pump a dye laser 29. Output of dye laser 29 is selected to cover a region of the visible spectrum so as to be substantially separated in wavelength from the spectral region of laser 12. One such laser which satisfies this requirement is a rhodamine 6-G dye laser which has a primary emission at approximately 598 nm. The output lines from dye laser 29 may be directed by means of internally reflecting prisms 23 toward lens 32 with a slight downward trajectory relative to the argon beam so as to be focused onto region 34 in the stream of flowing particles.

A nozzle 40, incorporated within flow cytometry device 10 of the present invention, facilitates the flowing of particles within the fluid stream 38. The utilization of a nozzle of this type is well-known and is described, for example, in U.S. Pat. No. 3,826,364. In the present device being described, the two laser-particle-stream intersections, designated by numerals 28 and 34, are spaced approximately 200-250 microns apart. The fluid stream later breaks into droplets 41 which may be deflected for cell sorting.

A particle flowing in stream 38 first flows through focused light region 28 after the particle emerges from nozzle 40. Unscattered laser light passing through light region 28 strikes the light-scatter obscuration bar 42 on the optical axis of the light-scatter channel. Scattered light, collected by the lens 44, passes through a first iris 45 which determines the maximum angle of scattered light collected. Following first iris 45 is a beam splitting mirror 46 which reflects a percentage of the incident light toward scatter detector 48, and transmits the remaining percentage of the incident light onto a light absorber (not shown). A second iris 49 functions as a field stop to restrict the source of scattered light to the point of intersection represented by focal region 28. After passing through filter 50, the scattered light is detected in detector 48. This detector functions electrically to assess the size of the particles flowing in the fluid stream according to well-known techniques. It is understood that the light scatter features herein described are merely included to round out the features of a typical flow cytometry device which may rely upon light scatter to obtain information from particles passing through the light beams.

In the embodiment of the present invention illustrated in FIG. 1, light from dye laser 29 is also directed at flowing stream 38 to focal region 34, which is vertically displaced from focal region 28 along the vertical axis of the stream. Light from the dye laser scattered by a particle is picked up by the scatter-channel optics, but is preferably blocked from detector 48 by the dielectric filter placed in the scatter channel.

With respect to the fluorescence channels, illumination provided by the different wavelength operation of the lasers is available for sequential excitation of fluorochromes having substantially separated emission spectra. At least one, but preferably two or more, immunofluorescent stains having different emission spectra are excited by the excitation energy provided by the light energy of each laser. As seen in FIG. 1, the two independent laser beams intersect stream 38 at focal regions 28 and 34 vertically spaced so that a particle crosses region 28 first, and then region 34. Accordingly, two pairs of optical signals may be generated by the particles passing through the light beams. These pairs of signals are preferably spaced in time by the time required for the particle to travel from the first beam intersection point to the second beam intersection point. This time spacing permits the pairs of signals to be separately analyzed giving signals proportional to the fluorescence emissions of the particles when excited at the two different excitation wavelengths. Fluorescence radiation emitted from the particles is directed around obscuration bar 54 which blocks refracted light from the separated beams. All fluorescence signals are focused by lens 55 near a first beam splitter 56. In the preferred configuration, beam splitter 56 is a high reflectance mirror positioned in the optical path in such a way that only emission from region 34 is intercepted and reflected, while emission from region 28 passes below beam splitter 56 into an alternate path.

Thus, fluorescence emitted by particles stimulated in light region 28, after passing beam splitter 56, then encounters a dichroic mirror 57. The purpose of dichroic mirror 57 is to separate two different colors traveling along the fluorescence light path so that they may be analyzed separately. For example, dichroic mirror 57 would be selected to separate, for example, the different color wavelengths of particles excited in region 28. In this instance, and merely for exemplary purposes, wavelengths in the green region would be transmitted through dichroic mirror 57 and then through a barrier filter 59 which is designed to transmit wavelengths of only one color region, in this instance, green. Green light then enters a fluorescence detector 60.

Light encountering dichroic mirror 57 in the yellow region, for example, would be reflected by the dichroic mirror through a barrier filter 61 which transmits wavelengths of only one color region in this case, yellow. A fluorescence detector 62 then receives this yellow light.

Light focused in light region 34 also provides excitation energy at a single wavelength sufficient to excite up to two fluorochromes different from those excited in light region 28. After the fluorescence emitted by the particles excited in light region 34 passes through lens 55 and is reflected off beam splitter 56, this light encounters another dichroic mirror 58. Similar to the description of dichroic mirror 57 above, the second dichroic mirror 58 is selected to separate the wavelengths of two different regions of the color spectrum. For example, both red and far red signals may be generated as a result of the particles passing through excitation region 34. Wavelengths in the red region would be transmitted through dichroic mirror 58 and then through a barrier filter 63 which is designed to transmit wavelengths of only the red region. This light is then directed to a fluorescence detector 64. Wavelengths in the far red region would be reflected by dichroic mirror 58 through a barrier filter 65, whereupon this light enters fluorescence detector 66. Accordingly, it can be seen that light from two lasers, each of which may excite two or more fluorochromes at the respective wavelengths of operation of each, allows the detection and quantification of multiple subpopulations of particles in a sample during a single pass of that sample in a flow cytometry device such as described.

Fluorescence detectors 60, 62, 64 and 66 are provided to preferably receive the four separated green, yellow, red and far red light paths, respectively. These fluorescence detectors may be low-noise photomultiplier tubes or the like which convert optical signals into electrical signals. Although not shown in FIG. 1, these electrical signals are then fed electrically to be processed by the electronics of the flow cytometry device for analysis or other purposes. Various displays, information presentation, accumulation or recordation may be provided in the flow cytometry device. Similarly, the particles having specific characteristics may be separated and sorted in accordance with the techniques taught in U.S. Pat. No. 3,826,364.

More details of the optical and light energy elements of the laser apparatus of the present invention may be seen by referring to FIG. 2, taken in conjunction with FIG. 1. It can be seen that long pass dichroic 18 intercepts the multi-line pump in the space between the pump head and the dye head. It is preferred that dichroic 18 be composed of a simple high-low dielectric stack of non-absorbing layers. The number of layers, of course, depends upon the design requirements of the apparatus. In the flow cytometry apparatus being described, the desired excitation line of the primary laser is preferably set at 488 nm, while the excitation line of the secondary, dye laser is set at 598 nm. To satisfactorily accomplish this, the transmittance through dichroic 18, for example at 514.5 nm, should be high so that the dye laser efficiency is not significantly decreased. Approximately ideal reflectance specifications would be between 10% and 15% at 514.5 nm, between 40% and 50% at 488 nm, and greater than 95% at 458 nm. One design which functions satisfactorily to meet the specifications includes a dichroic with a stack of between 11 and 15 non-absorbing layers, each made from titanium dioxide and/or silicon dioxide. With 3 watts of pump power, the resultant power levels of the various argon lines after reflection and transmission are illustrated in FIG. 2.

Reflecting prisms 21 are mounted within apparatus 10 so as to be turnable to adjust the position of reflected beam 19 onto diffraction grating 22. The diffraction grating is also adjustably mounted within the flow cytometry apparatus. It is preferred that the diffraction grating be a flat, reflection type with about 1500 to 2000 lines per millimeter. It may be either a ruled grating with a 500 nm blaze or a holographically recorded modulated grating. For instance, a Bausch and Lomb ruled grating with 1700 lines per millimeter provides efficiencies at 458, 488 and 514 nm of 86%, 84% and 77%, respectively, for linearly polarized light with the vector parallel to the grating lines. Accordingly, as seen in FIG. 2, the wavelength may be changed by simply rotating grating 22 about an axis parallel to the lines. Such rotation may be performed by an operator of the apparatus turning a simple micrometer lead screw as an external adjustment.

From grating 22, light is directed to a lens assembly, designated by numeral 24. This lens assembly includes a first air-spaced achromatic lens 25. Light is focused by this lens to a diffraction limited spot on a slit 26 whose width is preferably between two and three times wider than the $1/e^2$ width of the focal waist. In one preferred design, the lens focal length is 48 mm, the focal waist at 488 nm is approximately 20 microns and the slit width is approximately 50 microns. A second lens 27 is included in lens assembly 24 which can be adjusted so that the output beam divergence of the filtered laser line is appropriate for focusing simultaneously with the dye laser beam onto the stream of flowing particles 38 by means of lens 32. The monochromator optics, such as the prisms and lens entrance and exit surfaces, are all anti-reflection coated for 0.995 or greater transmittance at the argon wavelength. Further, the diffraction grating, whether a holographically recorded or ruled type, may be replicated on a copper substrate so that the energy densities, even with a 5.0 watt pump, should not present a threshold problem.

In order to appreciate how the diffraction grating of the present invention compares with a narrow line interference filter for nearby filtering, such as described by Arndt-Jovin et al., the slit-function half widths of the present invention may be compared with the bandwidth of narrow line interference filters. With a 1700 line per millimeter grating, the present system may have a half width of 0.5 nm and an 84% peak efficiency at 488 nm. An interference filter with a 10 nm half width normally has a peak efficiency of 40 to 50%. Such an interference filter with a 1 nm bandwidth has an efficiency of from 15 to 30%. Accordingly, the grating monochromator scheme of the present invention provides significantly higher efficiencies than interference filters. The preferred configuration of a diffraction grating with 1700 lines per millimeter and a 3.0 watt multi-line argon pump provides an output at 488 nm of approximately 320 mw, and at 598 nm from the dye laser of approximately 280 mw. With the same system, adjusting the primary line to 457.9 nm results in an approximate output of 150 mw, which is still quite respectable. If a 5.0 watt multi-line argon pump is used, over 500 mw at 488 nm and 598 nm, and over 250 mw at 457.9 nm, could be expected.

In order to stabilize the output of an argon laser, a diode monitoring and feedback system commonly referred to as "light control" is used. With this system, a small amount of light is picked off at the output of the laser and continuously monitored by a photodiode detector. The variation of this signal is then used as feedback to control the input current of the laser. Thus, in a multi-line mode, the total integrated output power is quite constant with time. However, when splitting off two separate lines as in the described invention, a major problem exists in that the output power of neither line, if taken separately, will necessarily follow the total power of all the lines taken together in the multi-line mode. To overcome this problem, optical pickoff elements are included for separately monitoring a small amount of the output light from each beam. These are depicted in FIG. 2. Thus, a small amount of reflected light 19 coming from diffraction grating 22, is picked off after passing through slit 26, and continuously monitored by a diode detector 75. In one preferred design, the multi-line pickoff at the laser output is removed, and the obseved intensity variations of photodiode 75 may be used to control the input current of multi-line pump 12. Accordingly, short wavelength excitation may be stabilized as a result of the feedback to the multi-line argon pump. For stabilizing the longer wavelength dye line, a small amount of the output beam of dye laser 29 is picked off and monitored by diode detector 77. The variation of the signal at detector 77 is fed forward to control the gain of photomultipliers 64 and 66 which are measuring emission from the secondary (dye laser) line. It should be noted that the roles of diode detectors 75 and 77 may be reversed, with the signal at 77 being used as feedback to control the input current of the multi-line laser 12, and the signal at diode 75 used to feedforward to vary the gain of detectors 60,62 and 48 (FIG. 1) which measure fluorescence and scatter from the short wavelength excitation line.

A further option retains the multi-line "light control" system of the pump laser 12, but in addition feeds forward from both separated beams to the appropriate detectors. Thus, pump laser 12 stabilizes itself with multi-line feedback before any beam splitting occurs, and relative fluctuations in single line output of the split beams are accommodated by feedforward from each single wavelength line. In this system, the output of photodiode 75 (FIG. 2) would feedforward to the gains of detectors 60,62 and 48 (FIG. 1), and the output of photodiode 77 (FIG. 2) would feedforward to the gains of detectors 64 and 66 (FIG. 1). Because the response of the laser output power as a function of changes in input current is rather slow, such feedforward systems could be expected to have performance advantages in terms of perceived stability over the usual feedback systems.

It should also be noted that instead of the fine line grating system as described herein, the dispersing system may also consist of several prisms arranged so that their dispersions add, and so that incident angles approach Brewster's angle, for high transmittance. However, it should be pointed out that such a prism system might tend to be more complicated and expensive, and might not provide as much linear dispersion as the preferred diffraction grating scheme.

In a typical application of the present invention for flow cytometry purposes, primary laser 12 may be adjusted to one of the visible argon lines between 457.9 nm and 514.5 nm, while secondary laser 29, utilizing a dye known as rhodamine-6-G, may be independently adjusted to output a line between 580 nm and 640 nm. For four color applications, the primary laser, set at 488 nm, excites two fluorochromes such as FITC and PE which emit fluorescence at 520 nm and 575 nm, respectively. The dye laser, independently set at 598 nm, excites two additional stains known as TR and A-PC with corresponding emission peaks at 625 nm and 660 nm.

Thus, the present invention provides a high dispersion, high efficiency monochromator scheme for separating spectral lines from the pump laser. This technique offers an economical method of creating a dual line excitation system for multi-parameter analysis. At the same time, the present invention offers performance advantages over previously known systems, which use interference filters, in terms of efficiency, ease of wavelength adjustment, stability and reliability.

What is claimed is:

1. A flow cytometry apparatus for determining characteristics of cells or the like flowing in a liquid stream comprising:

means for moving cells, substantially one at a time, in a liquid flow stream;

a first excitation light source for providing a first beam of light;

a dichroic element positioned in the path of said light beam for transmitting a portion of said light and for reflecting a portion of said light;

dispersive means for spectrally separating wavelengths of the light reflected by said dichroic element and directing said spectrally separated light toward said cells moving in said flow stream to provide a first area of illumination therefor;

a second excitation light source positioned to receive the light transmitted through said dichroic element and adapted to be driven by the energy of said transmitted light for producing a second beam of light which is directed toward said cells moving in said flow stream to provide a second area of illumination therefor;

means for detecting light associated with each moving cell as it passes through said areas of illumination; and means for using said detected light to determine one or more characteristics of said cells.

2. The apparatus of claim 1 wherein said first excitation light source is a laser which produces a beam of light at a plurality of spectral energy lines.

3. The apparatus of claim 2 wherein said laser is a multi-line argon pump laser.

4. The apparatus of claim 1 wherein said separating means is a diffraction grating adjustably positioned in the path of said reflected light so as to disperse wavelengths according to angle so that only one of such dispersed wavelengths is efficiently directed toward said moving cells.

5. The apparatus of claim 4 wherein said diffraction grating is a substantially flat plate having between 1500 and 2000 lines per millimeter.

6. The apparatus of claim 4 wherein said separating means further includes at least one achromatic lens and a slit through which light from said grating travels before striking the moving cells.

7. The apparatus of claim 1 wherein said second excitation light source is a laser which produces said second beam of light at a single wavelength.

8. The apparatus of claim 7 wherein the output wavelength of said second excitation light source is adjustable over a range of wavelengths.

9. The apparatus of claim 8 wherein said laser is a dye laser.

10. The apparatus of claim 9 wherein the output wavelength of said second beam of light is different from all of the light lines of energy produced by said first excitation light source.

11. The apparatus of claim 9 wherein the output wavelength of said second beam of light is lower in frequency than all of the light lines of energy produced by said first excitation light source.

12. The apparatus of claim 11 further including feedback means positioned in the light path of said second beam for monitoring the light output of said second excitation light source and feeding signals back to said first excitation light source for controlling stability of the output energy lines of said second excitation source.

13. The apparatus of claim 6 further including feedback means positioned in the light path past said slit for monitoring the dispersed light beam and feeding signals back to said first excitation light source for controlling stability of the output energy lines of said first excitation source.

14. The apparatus of claim 13 further including feedforward means positioned in the light path past said second excitation source for monitoring the light output of said second excitation light source and feeding signals forward to said means for detecting light for compensating for variations of the output energy lines of said second excitation light source.

15. The apparatus of claim 6 further including feedforward means positioned in the light path past said slit for monitoring the dispersed light beam and feeding signals forward to said means for detecting light to compensate for variations in energy of said dispersed light beam.

16. The apparatus of claim 1 wherein said means for detecting light includes a first device for detecting fluorescence emitted by the cells passing through one of said areas of illumination.

17. The apparatus of claim 16 wherein said means for detecting light includes a second device for detecting fluorescence emitted by cells passing through a second of said areas of illumination.

18. A dual laser excitation apparatus comprising:
a first laser for providing a first beam of light with a plurality of energy lines;
means for dividing said first beam of light into two portions;
dispersive means for separating spectral lines of one portion of said divided light beam and directing at least one of said spectrally separated lines to a first area of illumination; and
a second laser positioned to receive the other portion of said divided light beam and adapted to be energized so as to produce a second beam of light directed to a second area of illumination.

19. A flow cytometry apparatus for determining one or more characteristics of particles or the like flowing in a liquid stream comprising:
means for moving particles, substantially one at a time, in a liquid flow stream;
means for providing a first beam of light with a plurality of energy lines;
means for dividing said first beam of light into two portions;
dispersive means for separating spectral lines of one portion of said divided light beam and directing at least one of said spectrally separated lines toward said particles moving in said stream to provide a first area of illumination therefor;
means for receiving the other portion of said divided light beam and for being energized thereby to produce a second beam of light directed toward said particles moving in said stream to provide a second area of illumination therefor; and
means for detecting light with respect to each moving particle and for associating said detected light with one or more characteristics of each particle.

20. The apparatus of claim 19 wherein said means for providing the first beam of light is a first laser and said means for providing the second beam of light is a second laser.

21. The apparatus of claim 20 wherein the second laser provides a second beam of light at a single wavelength in the second area of illumination.

22. The apparatus of claim 21 wherein the means for separating includes means for dispersing said one portion of light so that the light which comprises said first area of illumination is at a single wavelength different from the single wavelength of light in the second area of illumination.

* * * * *